(12) United States Patent
Harris, Jr. et al.

(10) Patent No.: US 7,604,981 B1
(45) Date of Patent: Oct. 20, 2009

(54) EXCITABLE TARGET MARKER DETECTION

(75) Inventors: James S. Harris, Jr., Stanford, CA (US); Stephen J. Smith, Los Altos, CA (US); Evan P. Thrush, Sunnyvale, CA (US); Ofer Levi, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1216 days.

(21) Appl. No.: 10/384,166

(22) Filed: Mar. 7, 2003

Related U.S. Application Data

(60) Provisional application No. 60/362,750, filed on Mar. 8, 2002.

(51) Int. Cl.
*C12M 1/34* (2006.01)
*C12M 3/00* (2006.01)
*G01N 21/64* (2006.01)
*G01N 33/53* (2006.01)
*G01N 21/00* (2006.01)

(52) U.S. Cl. ........................ 435/287.2; 435/6; 435/7.1; 435/91.1; 435/91.2; 422/55; 422/82.05; 422/82.06; 422/82.07; 422/82.08; 422/50; 422/82.09

(58) Field of Classification Search .............. 422/82.05, 422/50, 55–58; 436/164, 165; 435/287.2
See application file for complete search history.

(56) References Cited

U.S. PATENT DOCUMENTS

| | | | | |
|---|---|---|---|---|
| 4,142,198 A | * | 2/1979 | Finnila et al. ............... 257/227 |
| 4,150,295 A | * | 4/1979 | Wieder .................... 250/458.1 |
| 4,195,932 A | * | 4/1980 | Popelka ...................... 356/407 |
| 4,442,444 A | * | 4/1984 | Osaka ........................ 257/186 |
| 4,518,255 A | * | 5/1985 | Zuleeg ...................... 356/5.08 |
| 4,716,559 A | * | 12/1987 | Hine ...................... 369/112.27 |
| 4,810,658 A | * | 3/1989 | Shanks et al. ............... 436/172 |
| 5,039,490 A | * | 8/1991 | Marsoner et al. ......... 422/82.01 |
| 5,200,634 A | * | 4/1993 | Tsukada et al. ............. 257/291 |
| 5,203,329 A | * | 4/1993 | Takatani et al. ............ 600/334 |
| 5,350,922 A | * | 9/1994 | Bartz ...................... 250/338.5 |
| 5,611,999 A | * | 3/1997 | Dosmann et al. ......... 422/82.05 |
| 5,633,724 A | * | 5/1997 | King et al. .................. 356/445 |
| 5,671,303 A | * | 9/1997 | Shieh et al. .................... 385/12 |
| 5,849,486 A | * | 12/1998 | Heller et al. .................... 435/6 |
| 5,914,976 A | | 6/1999 | Jayaraman et al. |
| 5,936,730 A | | 8/1999 | Foley et al. |
| 5,978,401 A | | 11/1999 | Morgan |
| 6,097,748 A | | 8/2000 | Huang et al. |
| 6,184,029 B1 | * | 2/2001 | Wilding et al. ........... 435/287.1 |

(Continued)

*Primary Examiner*—Jill Warden
*Assistant Examiner*—Neil Turk
(74) *Attorney, Agent, or Firm*—Crawford Maunu PLLC

(57) ABSTRACT

A variety of types of molecules are detected and/or analyzed using an integrated micro-circuit arrangement. According to an example embodiment of the present invention, a micro-circuit arrangement detects excitable target markers in response to an excitation source. The excitation source emits a first electromagnetic radiation to excite one or more target markers into emitting a second electromagnetic radiation. The excitation source and detector combination can be optimized to detect a specific characteristic of a biological specimen. In this manner, an excitation source can be combined with several optical-detectors or detection channels, where each optical-detector is measuring or sensing the same or different characteristic of the biological specimen.

10 Claims, 12 Drawing Sheets

U.S. PATENT DOCUMENTS

| | | | |
|---|---|---|---|
| 6,197,503 B1 * | 3/2001 | Vo-Dinh et al. | 435/6 |
| 6,344,664 B1 | 2/2002 | Trezza et al. | |
| 6,534,011 B1 * | 3/2003 | Karthe et al. | 422/82.01 |
| 6,867,420 B2 * | 3/2005 | Mathies et al. | 250/458.1 |

* cited by examiner

EXCITABLE TARGET MARKER DETECTION

RELATED PATENT DOCUMENTS

This patent document claims the benefit, under 35 U.S.C. § 119(e), of U.S. Provisional Patent Application Ser. No. 60/362,750, filed on Mar. 8, 2002.

STATEMENT REGARDING FEDERALLY-SPONSORED RESEARCH

Various embodiments disclosed in this patent document were made with support of the U.S. Government which, under Contract No. DARPA MDA972-00-1-0032, has certain rights therein.

FIELD OF THE INVENTION

The present invention relates generally to integrated micro-circuit arrangements, and more particularly to an integrated micro-circuit arrangements having a one-sided architecture for stimulating and sensing electromagnetic radiation.

BACKGROUND

The detection of biological species within complex systems is important for many biomedical and environmental applications, such as infectious disease identification, medical diagnostics and therapy, and biotechnology. There is a basic interest in the development of inexpensive techniques and portable biosensors for environmental and biomedical diagnostics. Of interest is developing new techniques and sensors, not only to selectively identify target compounds, but also to assay large numbers of samples. Problems remain in reproducibly detecting and measuring low levels of biological compounds conveniently, safely and quickly.

Varieties of sensing schemes have been developed for molecular detection, such as electrochemical, optical absorption, and interferometric sensing. Fluorescence sensing remains one of the most widely used methodologies in biotechnology. Separation technologies, for example capillary array electrophoresis and micro-array technology, use fluorescent labeling for the detection of analytes such as DNA and proteins. Fluorescence detection offers single molecule sensitivity and compatibility with standard biochemical reactions, such as polymerase chain reaction (PCR).

There are several methods for selectively identifying biological species, including antibody detection and assay (e.g., Enzyme-linked Immunosuppresent Assays, or ELISA) using molecular hybridization techniques. Joining a single strand of nucleic acid with a complementary probe sequence is known as hybridization. Generally, to identify sequence-specific nucleic acid segments, sequences complementary to those segments are designed to create a specific probe for a target cell, such as a pathogen or mutant cell. Nucleic acid strands tend to pair with their complements to form double-stranded structures. Thus, a single-stranded DNA molecule (e.g., a probe), in a complex mixture of DNA containing large numbers of other nucleic acid molecules, will seek out its complement (e.g., a target). In this manner, hybridization provides an accurate way to identify very specific DNA sequences, such as gene sequences from bacteria or viral DNA. Factors impacting the hybridization or re-association of two complementary DNA strands include temperature, contact time, salt concentration, degree of mismatch between the pairs, and the length and concentration of the target and probe sequences.

The probes are typically "labeled" for easier detection of the resultant biological species after hybridization. For example, labeling the probe with a radioactive tag or marker permits subsequent detection of the radioactivity to indicate probe-target hybrids. Radioactive labeling techniques, however, suffer from several disadvantages such as limited useful lifetime for the high-energy emission isotopes used. Another method to tag probes and/or mark target compounds uses visible and/or near-infrared (NIR) dye markers for non-radioactive detection (e.g., molecular or quantum dot based probes). When hybridized to their targets, the dye-marked probes are designed to exhibit fluorescent properties when excited by certain electromagnetic radiation (e.g., laser light, lamp light, or light emitting diode (LED) light), the fluorescence being detected optically. Intensity of the fluorescence is proportional to the presence of the dye-marked probes, and can be used for quantitative measurements, and further processing. Fluorescence detection is extremely sensitive for certain target compounds; for example, a zeptomole ($10^{-21}$ mole) detection limit has been realized using fluorescence detection of dyes with laser excitation. Implementation of a DNA chip based on high-density oligonucleotide arrays and fluorescence analysis is further described by Hacia et al. (J. G. Hacia, L. C. Brody, M. S. Chee. S. P. A. Fodor F. S. Collins) in Nature Genetics Dec. 14, 1996).

Despite efforts to develop chips for detection of biological species, there continues to be a need to improve implementations of micro scale detection systems for further convenience and portability. Furthermore, there continues to be a need for designs that accommodate efficient integrated circuit manufacturing techniques to realize associated cost savings.

SUMMARY OF THE INVENTION

The present invention is directed to an approach for micro detection/analysis of various molecule types, such as biological species, in a manner that address the aforementioned issues, as well as other related issues.

According to one aspect of the present invention, a micro-circuit detection arrangement includes an excitation source and at least one optical-detector coupled to a substrate arranged to form a pixel, with the pixel being further arranged in a planar array of pixels. The excitation source is adapted to emit a first electromagnetic radiation away from the substrate to excite a target marker into emitting a second electromagnetic radiation. A filter is optically coupled to the at least one optical-detector, the filter being arranged and configured to attenuate the first electromagnetic radiation from being sensed by the optical-detector, thereby achieving spectral separation. Alternatively, the optical-detector, or several optical-detectors, are arranged and configured to discriminate the second electromagnetic radiation by parameters such as temporal lifetime or intensity. The optical-detector is adapted to sense the second electromagnetic radiation and generate a detection signal in response to sensing the second electromagnetic radiation. With these approaches, excitable target markers, such as those discussed in the Background above, are detected.

According to another aspect of the present invention, a micro-circuit arrangement detects excitable target markers in response to an excitation source. The micro-circuit arrangement includes a plurality of optical-detectors and emission sources in proximity to one another and in a substantially planar distribution on a circuit foundation (e.g., in an array on a substrate), with assimilation circuitry monitoring each such optical-detector. The excitation source emits a first electromagnetic radiation to excite one or more target markers into emitting a second electromagnetic radiation. At least one filter is adapted to attenuate the first electromagnetic radiation from being sensed by the optical-detector arrangement. The optical-detector arrangement is adapted to sense the second electromagnetic radiation and generate detection signals in response to sensing the second electromagnetic radiation. The assimilation circuitry functions as a decoder to report data indicative of the likely target and/or reporting one of the optical-detectors. This reported data is then further analyzed manually or automatically through additional equipment such as a programmed CPU.

In another implementation, an excitation source is combined with several optical-detectors and/or detection channels, wherein each optical-detector is adapted for measuring and/or sensing the same or different characteristics of a biological specimen, such as spectral characteristics, excited state lifetime and fluorescent intensity. In one instance, these optical-detectors are tailored to sense different colors of radiation, which has been found particularly useful for multi-dye experiments.

In another implementation, a first optical-detector is adapted for measuring spectra of a biosample, a second optical-detector is adapted for measuring an excited state lifetime of the biosample (e.g., fluorescent lifetime measurement (FLIM)) and a third optical-detector is adapted for detection sensitivity (e.g., having a narrower spectral detection capability). With this approach, different characteristics of the biosample can be measured using optical-detectors that can be optimized for detecting a particular characteristic, which increases detection limits and adds system flexibility.

According to another example embodiment, an excitation source and optical-detector are adapted for detecting a specific characteristic of a biological specimen. In one implementation, one sensor (i.e., micro-circuit arrangement pixel) is optimized for high sensitivity and an adjacent sensor is adapted for measuring excited state lifetime.

These above-characterized aspects, as well as other aspects, of the present invention are exemplified in a number of illustrated implementations and applications, some of which are shown in the figures and characterized in the detailed description and claims that follow. However, the above summary of the present invention is not intended to describe each illustrated embodiment or every implementation of the present invention.

BRIEF DESCRIPTION OF THE DRAWINGS

The invention may be more completely understood in consideration of the detailed description that follows in connection with the accompanying drawings, in which.

Figure 1:
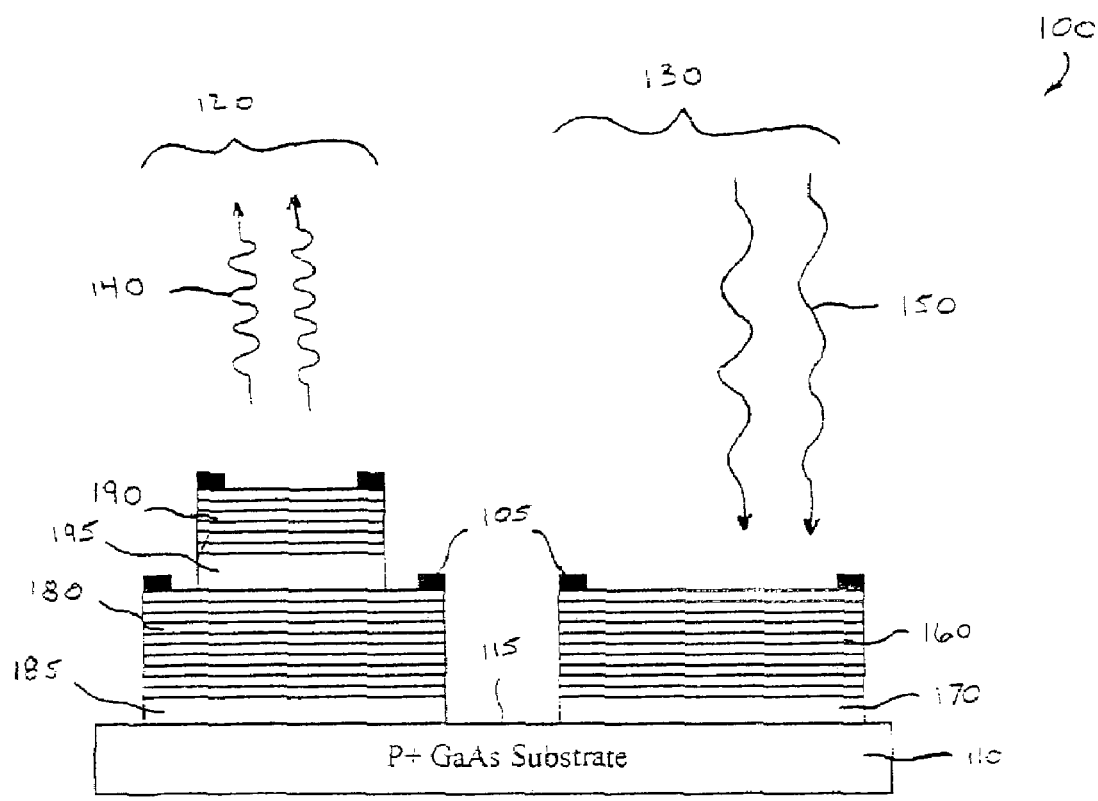
FIG. 1 illustrates a micro-circuit arrangement, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices and manufacturing methods. The invention has been found to be particularly suited for an integrated micro-circuit arrangement adapted to detect/analyze various types of molecules; one such example application is specifically directed to detecting/analyzing biological species via fluorescence sensing. While the present invention is not necessarily limited to such applications, various aspects of the invention may be appreciated through a discussion of various examples using this context.

One aspect of the present invention integrates semiconductor optoelectronics and/or micro-optics using an approach that can be useful, for example, to achieve one or more of the following: a relatively small detection system; lower manufacturing costs; and increased parallelism, portability and robustness. In one example embodiment of the present invention, optoelectronic emission sources (e.g., a light source) and optical-detectors for fluorescence detection are arranged in a planar array, the emission sources emitting and optical-detectors receiving electromagnetic radiation oriented in an approximately normal direction with respect to the planar array. The emission sources and optical-detectors are located in relatively close proximity on the common plane along which the array is formed (e.g., in a range of approximately 1 μm-1 mm apart). An interference filter is located over the optical-detector and/or optically coupled in close proximity to the optical detector.

According to one aspect, the present invention is directed to an integrated microchip biosensor device that employs multiple optical sensing elements (including emission and detection components) and processing microelectronics on a single integrated chip. The biosensor device is used in conjunction with one or more nucleic acid-based bioreceptors designed to detect sequence specific genetic constituents in complex samples. The microchip devices of the present invention combine integrated circuit elements, optical devices and optoelectronic devices in a self-contained, integrated micro-circuit arrangement having a single-sided operating architecture. Nucleic acid-based receptor probes are typically included in a biochip containing a biological sample.

According to various implementations of the present invention, the device incorporates one or more biochips for presenting/processing the biological sample, or the sensing apparatus is made portable to operate upon biochips that are independent from the device. The one-sided architectures of one or more of the example embodiments discussed herein essentially decouple the optoelectronic sensing from the biochip. For example, in transmission architecture schemes where the biochip is sandwiched between the emission sources and detectors, the biochip may need to be relatively transparent to the relevant wavelengths of light. The optical parameters of the biochips can be made less important by one-sided sensing schemes. Also, one-sided architectures can be easier to align than transmission sensing schemes because the alignment of the photodetectors, filters and excitation sources can be pre-aligned by micro fabrication processes. This approach can be particularly advantageous, for example, in applications where a disposable biochip is used.

According to another example embodiment, a fluorescence sensor includes one or more excitation (e.g., light) sources, one or more corresponding integrated filters/detectors arranged in a planar array with the excitation source to effect a one-sided sensing architecture, and signal amplification/processing circuits. Micro-optic circuits are used for directing, focusing and/or collimating an emission from the excitation source, and in some implementations, for collection of the dye emission. The signal amplification/processing circuitry is used to drive the excitation source, readout the signal generated at the detector and perform additional signal processing. A biochip is coupled to the fluorescent sensor in one example implementation, and is independent in another example implementation. In a further implementation, a biochip includes an arrangement for immobilizing one or more bioprobe(s).

In particular applications, a target nucleic acid is tagged or labeled with a substance that emits a detectable signal. Alternatively, a target is attached to an immobilized bioprobe that emits a detectable or altered signal when combined with the target nucleic acid. The tagged or labeled species may be fluorescent, phosphorescent, or otherwise luminescent, may emit Raman energy, and/or may absorb energy.

In another example embodiment, one or more of the sensors and arrangements discussed herein are used with flow channel schemes for detecting the presence of a molecule within the flow channel. According to one example implementation, sensors are arrayed across a linear array of flow channels, for example in an application such as capillary array electrophoresis. According to another example implementation, sensors are arrayed in an individual flow channel to enable the measurement of molecular flow rate in response to some stimulus such as diffusion or applied electric field, which may lead to additional information in the measurement.

According to one aspect, an integrated system is adapted for sensing a targeted nucleic acid sequence in combination with a biological probe. The probe is modified to receive light, or other electromagnetic radiation, of a first frequency and thereby caused to emit light, or other electromagnetic radiation, of a frequency different than the first frequency. The system emits the excitation light and detects the probe-emitted radiation by means of a photo-transducer. The target nucleic acid is typically a uniquely characteristic gene sequence of a pathogen such as a fungus, bacteria, or virus, or other distinct nucleic acid species, examples of which may be found in mutant mammalian cells or in individuals with inherited errors of metabolism. Alternatively, the target nucleic acid is modified or labeled to include a tag or marker that emits a signal (e.g., radiation) upon exposure to the incident light from the sensor system.

The target species may be immobilized directly on the biochip. The approach of the present invention avoids the need to have the biological sample in physical contact with the sensing system (i.e., the micro-circuit arrangement including the exciting source and sensing transducer) and is therefore attractive for simplifying large-scale production, and providing testing portability and re-usability.

According to one example application, target nucleic acid sequence is hybridized with a nucleic acid sequence that is selected for the particular nucleic acid sequence (e.g., bioprobe). As stated earlier, the selected bioprobe is immobilized on a suitable biochip substrate, the biochip being either coupled to or independent from the sensing system. The bioprobe is labeled with a tag that is capable of emitting light or other non-radioactive energy. Upon hybridization with a target nucleic acid sequence, the hybrid product is irradiated with light of suitable wavelength and caused to emit a signal in proportion to the amount of target nucleic acid hybridized. According to one application, the labeled bioprobe comprises a labeled molecular bioreceptor chosen for their known ability to selectively bind with the target nucleic acid sequence. In certain particular examples, the bioreceptor itself may exhibit changes in light emission when its cognate is bound. In other applications, the amount of target nucleic acid that is hybridized is increased when only trace quantities are present in a biological sample. In another implementation, polymerase chain reactions (PCRs) are used in connection with DNA analysis to amplify DNA sequences.

According to another aspect, light of a highly directional or focused nature is impinged on a target nucleic acid that, inherently or by virtue of an appropriate tag or label, emits a detectable signal upon irradiation. The irradiation is provided by a suitable light source, such as a laser beam or a light-emitting diode (LED). The incident light is segregated from the light emitted from the biosample using one or more techniques including providing different light paths (i.e., spatial filtration), using micro-optics for directional control of incident and excited light and/or employing appropriate optical filters to attenuate the incident light from the detector. In this regard, various implementations of the present invention are directed to using one or more of Raman, fluorescence and phosphorescence detection modes.

The micro-circuit arrangements discussed herein may be formed using one or more of a variety of techniques. According to one example approach, at least one excitation/emission source is bonded onto a silicon-based platform (e.g., an integrated circuit), the platform including filters, detectors and control circuitry formed therein. In another example approach, excitation sources of different wavelengths are bonded upon a common substrate and used in applications employing multiple tags or labels within a common biological sample. In another example approach, at least one organic-based emission source is bonded onto a silicon-based platform, the platform including optical-detectors, filters and control circuitry formed therein.

According to another example embodiment, a micro-circuit arrangement such as that discussed herein is formed by bonding at least one emission source and corresponding silicon-based optical-detectors onto a silicon-based integrated circuit platform. In one implementation, the micro-circuit arrangement is formed by bonding at least one emission source, corresponding optical-detectors, and any necessary electronic circuitry onto a glass, plastic or quartz platform, thereby allowing for a transparent substrate. In each above-mentioned approach, an emission-specific filter is integrated onto the optical-detector during fabrication of the optical-detector.

According to another example embodiment of the present invention, fluorescence sensor components are monolithically integrated, e.g., rather than being formed independently and subsequently bonded together by some method. At least one emission source, corresponding optical-detector(s) and filter(s) are monolithically integrated on a common substrate. In some schemes, the driving, readout and processing circuitry is monolithically integrated as well.

In one implementation, the monolithically-integrated components discussed above are formed using deposition techniques including one or more of: sputtering, e-beam, evaporation, thermal evaporation, or similar deposition techniques to create layers. Thereafter, implantation and other methods are used to create regions within the layers, and etching or other means for removing portions of deposited layers are used to form a monolithic integration circuit arrangement. Also, epitaxial growth methods can be used such as molecular beam epitaxy (MBE), metal-organic chemical vapor deposition (MOCVD) and liquid phase epitaxy (LPE).

A variety of material systems are applicable for implementing particular aspects of the present invention. For example, AlGaAs is useful for forming optoelectronic components; wide band gap III-V and II-VI semiconductor materials such as ZnSe and GaInN are useful for forming visible spectrum LEDs and VCSELs; low band gap III-V and II-VI materials such as GaInNAs, InP, GaInAs, and GaInAsP are useful for extending photo detection absorption to longer wavelengths in the infrared; silicon is useful for manufacturing electronic and optical-detector components; glass/quartz substrates are useful when substrate transparency is a problem; and organic light emitting materials are useful for manufacturing certain excitation sources.

According to another example application, one or more of the micro-circuit arrangements are utilized for near-infrared fluorescence detection. This spectral range is compatible with standard AlGaAs optoelectronic technology for forming sensor components and benefits from the reduced background fluorescence from complex bio-fluids such as blood. In analyzing complex bio-fluids, such as blood, near-infrared dyes have a significant advantage over visible dyes due to low background fluorescence of biological samples in the infrared portion of the spectrum.

For multi-color tag experiments, it has been discovered that it is advantageous to have an optical-detector material that has a much smaller bandgap than the material for the excitation source. This approach has been found useful with quantum dots labeling experiments, where one laser can be used to excite many quantum dots. In this regard, another example embodiment is directed to an excitation source emitting a wavelength around 400 nm that is used in conjunction with corresponding Silicon optical-detectors that have a bandgap of about 1.1 microns. This enables the detection of many unique quantum dots from about 400-1000 nm.

In another example embodiment, time-decay fluorescence is used to detect a plurality of tags. In this example approach, labels are tailored to have a variety of excited-state lifetimes. The fluorescent lifetime of a label acts as a marker (e.g., instead of discriminating based on corresponding tag emission spectral information). In one instance, a plurality of optical-detectors (e.g., imaging sensors) are used wherein first and second ones of the optical detectors are adapted for detecting fluorescence decay at first ($t_1$) and second ($t_2$) time intervals. Depending on the application, this approach may greatly simplify the micro-circuit configuration because multi-tag detection is accomplished using relatively few wavelengths (e.g., as compared to other methods and approaches, such as some color discrimination approaches).

FIG. 1 illustrates a micro-circuit arrangement 100 adapted for detecting excitable target markers, according to another example embodiment of the present invention. Micro-circuit arrangement 100 includes a substrate 110, a light emitter 120 (i.e., an excitation source) and filter/optical-detector 130. The light emitter 120 and filter/optical-detector 130 are coupled to the substrate 110, for instance, using a scheme such as hybrid scheme or a monolithic integration scheme. In one implementation, additional driver/processing circuitry is implemented on the substrate 110 for use in the operation of the light emitter 120 and/or the filter/optical-detector 130.

Emitter 120 is a source of electromagnetic radiation, such as a laser or LED, designed to excite a target marker into fluorescence. The emitter 120 is coupled to a substrate surface 115 and, according to one example implementation, emits a first electromagnetic radiation 140 in an approximately normal direction away from substrate surface 115 and toward a target marker. In response to being excited by the first electromagnetic radiation 140, the target marker exhibits fluorescence, emitting a second electromagnetic radiation 150, at least a portion of which is directed back toward substrate 110 and is detected at the filter/optical detector 130. Second electromagnetic radiation 150 has at least one detectable characteristic that is distinguishable from first electromagnetic radiation 140, for example, a different frequency from first electromagnetic radiation 140.

Each of the emitter 120 and filter/optical-detector 130 may be implemented in a variety of manners. For example, the filter/optical detector 130 can be implemented using a filter disposed over a photo-diode. Other selected approaches are discussed below in further detail.

The example filter/optical-detector 130 of FIG. 1 includes at least one optical-detector 170 coupled to the substrate surface 115 in proximity to the excitation source 120, and arranged in a common plane with excitation source 120. In one implementation, light scattered and/or reflected back into the optical-detector 170 (e.g., not only from an associate light source, but also from adjacent light sources) is filtered by filter 160 to attenuate and/or block electromagnetic radiation at the detector surface. This scattering/reflecting of light may result from placing an optical-detector in relatively close proximity to a light emitter (i.e., emitter 120), arranging the optical-detector and light emitter in a planar array, and/or using a plurality of such detector-emitter arrangements together on a single chip. In addition, excitation light may be scattered from optical interfaces (e.g., micro-optics), as well as from the biological sample.

Optical-detector 170 is adapted to sense the second electromagnetic radiation 150 and, in response, to generate a detection signal (e.g., for readout by an electronic circuit arrangement, not shown in FIG. 1) for further processing.

Optionally, filter 160 is optically coupled to (e.g., physically coupled to, or integrally formed upon, as shown in FIG. 1) the optical-detector 170. Filter 160 is arranged and configured to attenuate the first electromagnetic radiation 140 from being sensed by the optical-detector 170. Filter 160 is located directly upon the optical-detector 170 and adapted to eliminate any chance of unfiltered light from reaching the optical-detector without first passing through the filter. This arrangement with the filter 160 being directly upon the optical-detector 170 may be achieved, for example, by locating the filter directly on the optical-detector. The filter 160 includes, for example, one or more of a variety of filter types such as low-pass, high-pass and/or band-pass filters.

According to another example implementation having certain features similar to those illustrated in FIG. 1, an excitation source and photo detector respectfully emit and collect their associated electromagnetic radiation through the substrate 110 in a bottom-emitting configuration. With this approach, micro-optics can be implemented directly on the back of a substrate, with the substrate formed to permit emitted and fluorescence electromagnetic radiation to pass therethrough. This implementation also operates in a one-sided manner with light being emitted from and collected by a common substrate surface.

Referring again to FIG. 1 and according to another example implementation, the emitter 120, filter and/or optical-detector(s) 130 are bonded to one surface of the substrate 110 (i.e., in a one-sided structure). According to another example implementation, the emitter, filter and/or optical-detector(s) are integrally formed in a monolithic structure upon the substrate. Other example implementations use a combination of forming certain components of an integrated circuit by monolithic integration and bonding other discrete components to the resulting integrated circuit.

One-sided sensing approaches such as shown in and discussed in connection with in FIG. 1 and elsewhere herein have been found to be particularly useful, for example, in fluorescent applications due to the elimination of a need for shining the excitation source (e.g., light) directly into the filter/optical-detector(s), giving spatial filtration. With this approach, fewer constraints are placed upon the filter than for transmission-type architectures. In addition, the biochip used with the one-sided micro-circuit arrangements discussed herein need not necessarily be transparent to the emission and excitation light; therefore, the biochip can be made of a relatively wide range of material compositions.

In another implementation, the one-sided architecture is implemented in a manner such that external alignment of a light emitter and filter/optical-detector is not necessary. In this implementation, and referring to FIG. 1 as an example, the light emitter 120 and the filter/optical detector 130 are fabricated to be in alignment (e.g., for a biochip located some range away from the micro-circuit arrangement).

According to another example embodiment of the present invention, emitter 120 of FIG. 1 is a light emitting diode (LED). This example embodiment is implemented using LEDs for applications utilizing quantum dots, rather than applications dependent on dye-based fluorescence, since LED emission characteristics can significantly overlap dye emission characteristics. However, implementing the emitter 120 using LEDs has been found particularly useful in applications where distinguishing characteristics between stimulus and fluorescence radiation is available. According to a more particular implementation, resonant cavity LEDs having a narrower spectral output are used to increase the sensitivity (specificity) of this approach and facilitate applications using dye-molecule based fluorescence.

Various optical-detector technologies can be used in connection with one or more of the approaches and micro-circuit arrangements discussed herein, including PIN, PN, metal-semiconductor-metal (MSM), photoconductivity and CCD (charged-coupled device) optical-detectors. In some implementations, the gain of the optical-detector(s) is increased to increase the sensitivity thereof. In various applications, avalanche optical-detectors (APDs), on-chip preamplifiers and/or photo-transistors are used to provide relatively higher gain to increase optical-detector sensitivity, for example, in high-bandwidth applications as discussed above. In another implementation, a resonant cavity optical-detector (RCPD) is used to filter out background electromagnetic radiation from the excitation source (i.e., high extinction).

In another example embodiment of the present invention, one or more of the filters discussed herein is adapted to reduce noise caused by the emission background (i.e., stray electromagnetic radiation from an emission source). In various implementations, the emission background is reduced using one or more of attenuation, absorption, and filtration. For example, as discussed above in connection with FIG. 1, the first electromagnetic radiation 140 can be filtered such that the signal detected at the optical detector 170 is not affected thereby. In one implementation, electromagnetic radiation including radiation 140 reflected back from a target biological sample and ambient radiation 140 from other emitters in the vicinity of filter/optical-detector 130 is removed. Such removal facilitates the optical-detector 170 being more sensitive to the second electromagnetic radiation 150 created by a target marker excited by emissions of emitter 120. Using a filter such as filter 160 at the detector rather than at the source has been found to be particularly useful in small-scale systems where the emission source and detector are in close proximity.

According to another example embodiment, a micro-circuit arrangement utilizes a mesa detector that is exposed from the sides as an optical detector for detecting electromagnetic radiation from a target marker. Absorbing and/or reflecting material (e.g., a metal layer) is formed and/or placed around the optical-detector sides (i.e., an active region). In one instance, an arrangement includes diffused junction photodiodes formed within an absorbing substrate. In one implementation, the micro-circuit arrangement is implemented in a transceiver application, wherein light is transmitted from a source at one end of a communication channel. The source light is sensed at a detector including a mesa detector at a remote end of the communication channel.

In another implementation, a micro-circuit arrangement including a mesa detector as discussed above is adapted for duplex communications. Each end of a communication channel is equipped with a source and detector. In one approach, the sources at each end of the communications channel emit electromagnetic radiation having similar or identical characteristics, and the detectors are configured to sense the common-emitted electromagnetic radiation. Physical segregation of the respective electromagnetic radiation signals emitted from each end is used to establish correspondence between a detector and an associated remote source, and to prevent a local detector from sensing electromagnetic radiation from an adjacent source (e.g., a source at the same end of the communication channel).

According to another example embodiment of the present invention, optical-detectors are used to distinguish electromagnetic radiation emitted from remote and proximate sources having a distinguishable electromagnetic radiation characteristic. A local light source emits a first electromagnetic radiation towards a remote point. A second electromagnetic radiation is emitted from the remote point back towards an optical detector located proximately to the local light source. The second electromagnetic radiation includes at least one characteristic that is distinguishable from the first electromagnetic radiation. The local optical-detector and an associated filter are configured and arranged to sense the second electromagnetic radiation and reject the first electromagnetic radiation. Specificity is achieved, for example, using one or more of: physical configuration (e.g., segregation of the second electromagnetic radiation from the first electromagnetic radiation), filtering, and optical-detector fabrication approaches. Filtering approaches that may be used in connection with this example embodiment include, for example, spectral filtering, time domain filtering, spatial filtering and filtering based on other properties where the received electromagnetic radiation (e.g., fluorescent tag emission radiation) differs from the source electromagnetic radiation (e.g., excitation).

In one example application related to the example embodiment discussed in the previous paragraph, the remote source is a biological target marker that is adapted to emit the second electromagnetic radiation as fluorescence. In another application, the remote source is fabricated similarly to the local source, but adapted to emit the second electromagnetic radiation rather than the first electromagnetic radiation. Because the local optical-detector/filter is designed to be specific to the remotely-generated second electromagnetic radiation and not the locally-generated first electromagnetic radiation, the channel between local and remote source/detector arrangements can propagate both the first and second electromagnetic radiation without physical segregation. In a transceiver application, for example, one fiber optic channel carries first and second electromagnetic radiation signals between local and remote ends.

In another example embodiment of the present invention, a micro-circuit arrangement is adapted for detecting target markers in CCD technologies and/or other silicon-implemented detector technologies, with an absorption and/or interference-based filter implemented in connection with an optical detector. In certain applications, spectral filters having a high optical index are implemented to reduce angular sensitivity of the target marker detection.

According to another example embodiment of the present invention, a filter arrangement is formed using a monolithic integration approach, wherein a mirror of a laser light source (or, e.g., the resonant cavity of an LED light source) is utilized as a filter for an optical-detector. In one implementation, additional depositions of dielectrics or semiconductor layers are used to modify the filter's characteristics. For example, additional depositions can be used to create unique band pass filters on top of particular optical-detectors, and used in multi-dye applications so that optical-detectors are formed to distinctly detect different colors (each corresponding to one or more unique dyes). In another implementation, the filter structure is deposited onto an emitter and selectively removed from the emitter (area) to permit the excitation emission to propagate out. In still another implementation, selected layers are etched to achieve the selective removal to modify the performance of the filter. In another implementation, the dielectric filter transmits the excitation emission (e.g., such that the above etching is not necessary).

According to another example embodiment of the present invention, an optical-detector is grown underneath an emission device, such as a vertical cavity surface-emitting laser (VCSEL) or resonant cavity LED. The optical-detector utilizes a bottom mirror of the VCSEL or resonant cavity LED as an optical filter to achieve a high quality optical-detector. This results in reduced costs and higher yield when compared to other integration schemes.

In one implementation, the approach in the above paragraph involves fabricating an extremely high quality optical-detector and an AlGaAs distributed Bragg reflector (DBR) filter. Typical AlGaAs DBRs or interference filters that have been found to be beneficial for use in connection with one or more of the example embodiments discussed herein can be grown to be at least 99.99% reflecting. Due to the high index of AlGaAs, the angular sensitivity of the DBR is drastically reduced. In one instance, spatial filtration is implemented in conjunction with the AlGaAs DBR filter to achieve higher sensitivity.

Referring again to FIG. 1 and according to another example embodiment, emitter 120 is a micro laser such as a VCSEL (discussed above) monolithically integrated along with a filter/optical-detector 130. The emitter structure (e.g., VCSEL epi-layer) includes two mirrors (or DBRs) and, in one implementation, a first N-doped DBR 180 and a second P-doped DBR 190. The mirrors are separated by a quantum well, laser gain region 195. Region 185 lies between the first N-doped DBR 180 and the substrate 110; in one implementation, region 185 includes intrinsic GaAs and in another implementation, region 185 includes doped GaAs. Implementing micro-circuit arrangement 100 using VCSELs facilitates parallel sensing architectures utilizing a plurality of closely-arranged micro-circuit arrangements in a common plane.

According to one example implementation, a simple PIN filter/optical-detector 130 is located adjacent to the VCSEL discussed above by adding an intrinsic GaAs region underneath the standard VCSEL epitaxial structure. The PIN optical-detector utilizes the N-doped DBR, discussed above, as both an emission filter 160 and electrical contact 105. In one instance, the PIN optical-detector epitaxial layer structure is grown using molecular beam epitaxy (MBE). A liftoff process is used to define the top ring contact 105. Deep reactive ion etching is then used to electrically isolate adjacent detectors by etching into the P+substrate, forming mesa structures (e.g., as discussed above). After the etching exposes the perimeter of an active region, dark current is extremely sensitive to processing parameters; therefore, oxidation of the optical-detector sidewalls is avoided to maintain the optical-detector dark current as low as possible. In one instance, surface passivation methods, such as sulfur passivation, are utilized to reduce the dark current even further.

Figure 2:
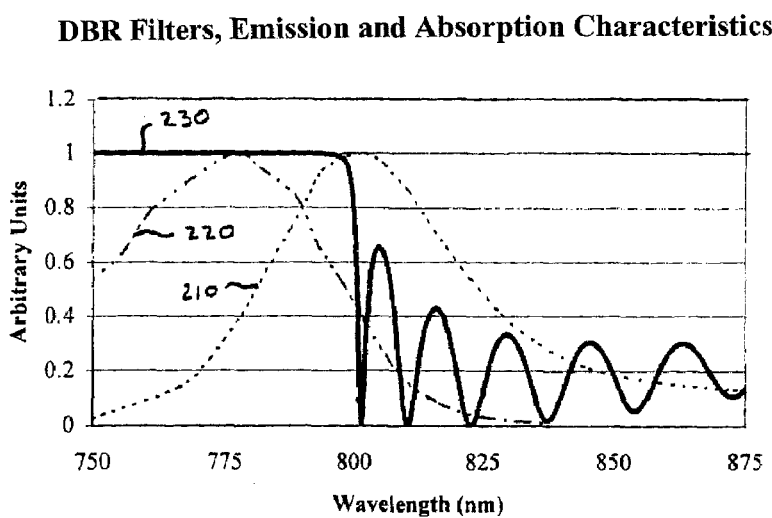
FIG. 2 is a graph of spectral characteristics of a filter and fluorescent dye emission/excitation for a micro-circuit arrangement, according to another example embodiment of the present invention.

FIG. 2 shows the emission/absorption characteristics of a fluorescent label (i.e., target marker, or dye) and the reflectivity spectrum of a DBR mirror, according to another example embodiment of the present invention. The DBR filter can be used both as a mirror for the laser and filter for the photodetector. Emission characteristics are shown by curve 210, absorption characteristics by curve 220, and reflectivity by curve 230. The DBR spectrum rolls off and allows detection of the Stokes' shifted photons from the dye. The AlGaAs VCSEL lazes in the near-infrared (NIR) regime (e.g., 750-800 nm) and is compatible with a number of near-infrared dyes that have absorbency peaks, for example, in the range 750-800 nm, and emission peaks in the range of 780-830 nm. In one implementation, the emission peak of the dye is selected to be less than about 830 nm to achieve efficient collection of the fluorescence. In other implementations, materials with lower band gaps are used as the detector active layer, such as III-IV materials with lower band gap, InGaAs or GaInNAs material systems. In another implementation, commercially available dyes (for example, IR-800 developed by Li-Cor Inc.) are used for protein and DNA analysis.

According to a more particular example embodiment of the present invention, an optical detector (e.g., optical detector 130 of FIG. 1) is implemented as a PIN photodiode having a double heterostructure and that achieves near 100% quantum efficiency over most of the dye emission spectrum. The spectral response of the photodiode is exemplified by the DBR spectrum, as discussed below. In one implementation, the PIN photodiode exhibits low dark current of less than about 1 nA/cm$^2$, which results in relatively low dark current noise and facilitates large area photodiode architectures, such as in the proximity architecture discussed below. For instance, optical-detectors exhibiting extremely low values of dark current (e.g., less than 10 nA/cm$^2$) and low detector series resistance (e.g., less than 50 ohms for 25 μm diameter using N DPR doping and 40 pair DBR of $Al_{0.3}Ga_{0.7}As/Al_{0.98}Ga_{0.02}As$) provide excellent sensitivity when appropriately filtered to remove excitation emissions as discussed herein.

The design of the optical-detector discussed in the above paragraph is adapted to allow various widths and intensity values appropriate to the configuration of the micro-circuit and application thereof. For instance, the response of the optical-detector is very linear over 9 orders of magnitude for optical powers ranging from approximately $10^{-9}$ mW to nearly 1 mW. The average quantum efficiency of the optical-detector is approximately 85% over the spectral range of 800-870 nm. In one implementation, the filtration (e.g., using filter 160 of FIG. 1) at the lasing wavelength can be as high as $10^5$ for a 40 pair DBR. The angular dependence of the filter is significantly reduced by the high index of refraction of AlGaAs material system. This filtration level is maintained over a reasonably large numerical aperture (e.g., 0.7 or greater) by shifting the lazing wavelength to the blue side of the DBR. According to one such example design, this filtration is effected over a numerical aperture of about 0.65. Referring to FIG. 2, the DBR reflectivity side lobes reduce the quantum efficiency of the detector to around 40 percent. Other implementations of the present invention utilize different filter and/or mirror designs to eliminate these side lobes and increase quantum efficiency.

Figure 3:
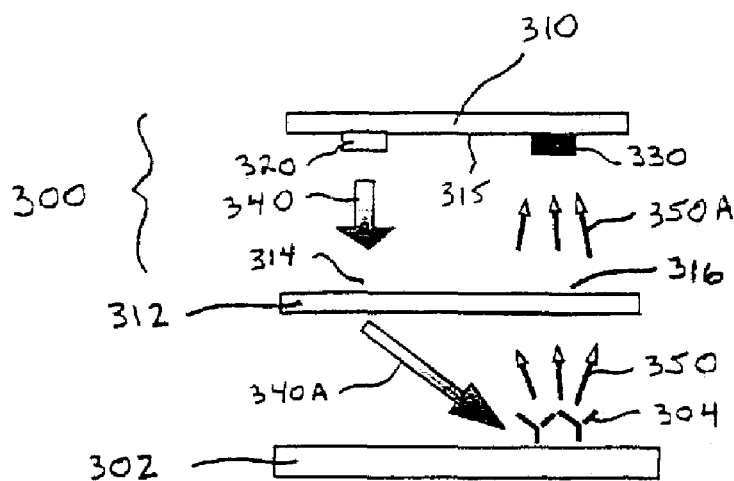
FIG. 3 illustrates a micro-circuit arrangement in an imaging configuration, according to another example embodiment of the present invention.

FIG. 3 illustrates another example embodiment of the present invention, wherein a micro-circuit arrangement 300 includes imaging architecture (e.g., a confocal architecture) for detecting excitable target markers. Features similar to those shown in FIG. 1 are indicated in FIG. 3 and subsequent figures using similar reference numbers, with certain description thereof omitted for brevity. For example, substrate 310 of FIG. 3 may correspond to substrate 110 described previously in connection with FIG. 1.

Micro-circuit arrangement 300 includes a substrate 310 having a substrate surface 315. An excitation source 320 is coupled to the substrate surface 315 and adapted to emit a first electromagnetic radiation 340 away from the substrate 310 towards a biochip 302. The electromagnetic radiation 340 excites a target marker 304 into emitting a second electromagnetic radiation 350 generally back towards substrate 310. A filter/optical-detector 330 includes at least one optical-detector and a filter optically coupled to a common substrate. Filter/optical-detector 330 is coupled to the substrate surface 315 in proximity to the excitation source 320 and arranged in a planar array with the excitation source 320. Filter/optical-detector 330 is adapted to filter, attenuate and/or discriminate against the first electromagnetic radiation 340 (and 340A), sense the second electromagnetic radiation and generate a detection signal responsive to sensing the second electromagnetic radiation.

A micro-optics refractive and/or diffractive structure 312 is interposed between substrate 310 and biochip 302 (e.g., having target marker 304), and used to perform directing, focusing and/or collimating of excitation emissions or collection of fluorescence. The micro-optics structure may be fabricated from a quartz wafer, the wafer having lenses formed on one or two sides. Fabrication is possible using standard photolithography procedures for up to micron size features, or e-beam lithography for smaller features such as diffractive lens and grating designs using sub-wavelength features to yield a high efficiency.

Micro-optics structure 312 includes a first micro-optics arrangement 314 optically coupled between the excitation source 320 and the target marker 304, for example by wafer bonding to the optoelectronics (e.g., emitter and/or optical-detector). The first micro-optics arrangement is configured to direct, focus or collimate the first electromagnetic radiation 340 from the excitation source towards the target marker 304. For clarity, optically redirected first electromagnetic radiation 340 is shown in FIG. 3 as 340A; however, electromagnetic radiation 340 and 340A are the same energies. According to one more particular implementation, emitter 320 is a VCSEL and first electromagnetic radiation 340 is laser light.

Target marker 304 (e.g., a dye) is combined (i.e., attached) with a target biological specimen such as a DNA fragment of interest (not shown). Target marker 304 is excited by first electromagnetic radiation 340 and exhibits fluorescence, emitting a second electromagnetic radiation 350, generally directed back towards substrate 310. Micro-optics structure 312 includes a second micro-optics arrangement 316 optically coupled between the target marker 304 and filter/optical-detector 330. The second micro-optics arrangement is configured to collect by focusing or collimating the second electromagnetic radiation 350 and directing it towards the filter/optical-detector 330 for detection and subsequent signal generation. For clarity, optically redirected second electromagnetic radiation 350 is shown in FIG. 3 as 350A; however, electromagnetic radiation 350 and 350A are the same energies and corresponding to the fluorescence of target marker 304.

According to other implementations of micro-circuit arrangement 300, only one of the first or second micro-optics arrangements 314 and 316 is used and is adapted either to direct, focus or collimate the first electromagnetic radiation 340 toward the target marker or collect and direct, focus or collimate the second electromagnetic radiation 350 toward the optical-detector (or filter). According to another aspect of the present invention, the micro-optics structure is coupled to the overlying substrate (such as 310).

For one particular implementation of filter/optical-detector 330, the DBR filtration is on the order of $10^5$, which is inadequate for high sensitivity applications. In this implementation, the design of the micro-optics structure is tailored to reduce the laser background even further via spatial filtration. Spatial filtration reduces the laser intensity at the detector by at least two orders of magnitude. In one implementation, direct specular reflection of excitation light into the detector 330 is avoided. The asymmetric configuration of FIG. 3 has been found to be particularly useful in this regard, where the excitation light does not reflect off the biochip surface directly into the detector/filter arrangement. In one implementation, the optical designs are optimized to allow angular intensity distribution at the detector plane to match the detector DBR acceptance angle, thereby minimizing the excitation light entry into the detector 330. These design concepts (spatial filtration, DBR acceptance angle) are applicable to some or all of the optical system designs for the arrangements discussed herein.

In another implementation, the filter/optical-detector 330 is implemented in applications susceptible to noise, such as scattered background emissions. In this implementation, imaging schemes that are less susceptible to scattered background emissions are implemented in connection with the filter/optical-detector 330. In one example, pinhole optical-detectors and/or confocal architectures are implemented with the filter/optical-detector 330.

Figure 4:
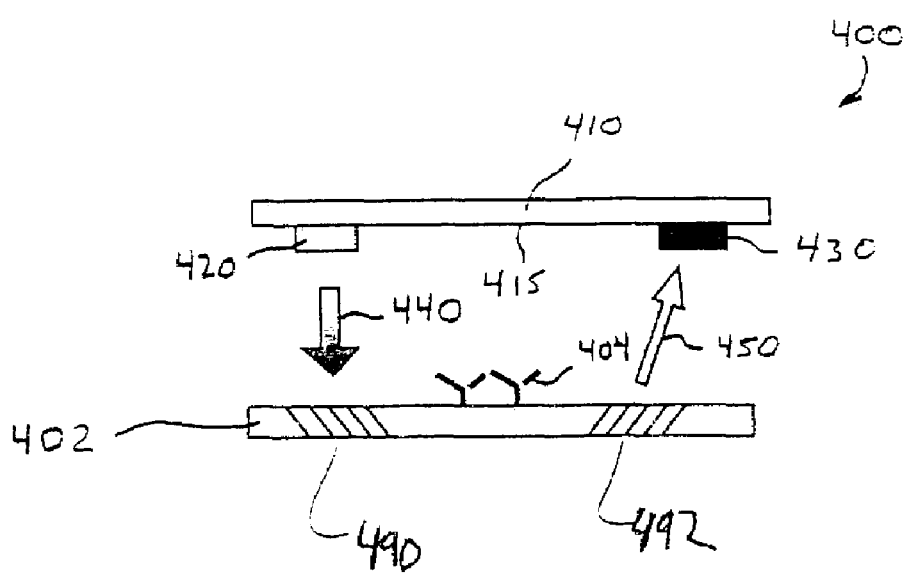
FIG. 4 illustrates a micro-circuit arrangement in a waveguide/grating configuration, according to another example embodiment of the present invention.

FIG. 4 shows a micro-circuit arrangement 400 having a waveguide architecture for detecting excitable target markers, according to another example embodiment of the present invention. Micro-circuit arrangement 400 includes a substrate 410 having a substrate surface 415. An excitation source 420 is coupled to the substrate surface 415 and adapted to emit a first electromagnetic radiation 440 away from the substrate 410 towards a biochip 402. The first electromagnetic radiation 440 excites a target marker 404 into emitting a second electromagnetic radiation 450 generally back towards substrate 410.

A filter/optical-detector 430 includes at least one optical-detector (not individually shown in FIG. 4) and a filter optically coupled to the optical-detector (not individually shown in FIG. 4). Filter/optical-detector 430 is coupled to the substrate surface 415 in proximity to the excitation source 420 and arranged in a planar array with the excitation source 420. Filter/optical-detector 430 is adapted to filter first electromagnetic radiation 440, sense the second electromagnetic radiation 450 and generate a detection signal responsive to sensing the second electromagnetic radiation.

Biochip 402 includes waveguide feature 492 for collecting second electromagnetic radiation 450 energy generated by the excited target marker 404, channeling it and ultimately directing it back towards filter/optical-detector 430. The waveguide architecture utilizes gratings to couple the first electromagnetic radiation 440 (e.g., a laser beam) into a waveguide feature 490, where the evanescent tail of the waveguide mode excites a biological sample. Then, the fluorescence is collected by the waveguide 492 and coupled out onto the filter/optical-detector 430. According to a further embodiment of the present invention, a micro-optics structure is used in conjunction with the waveguide architecture to further direct the first and second electromagnetic radiation.

In one example implementation of micro-circuit arrangement 400, the waveguide features 490 and 492 have an evanescent waveguide architecture, wherein the evanescent tail probes typically the first 100-200 nm from the waveguide surface. This approach has been found to be particularly useful when combined with affinity-based technologies, where an analyte can be attached to the waveguide surface. Typically, waveguide architectures require more laser power because only the evanescent tail of the waveguide mode excites fluorescence. Using this approach in connection with high numerical aperture waveguides, emitted photons can be collected with a high efficiency.

Figure 5A:
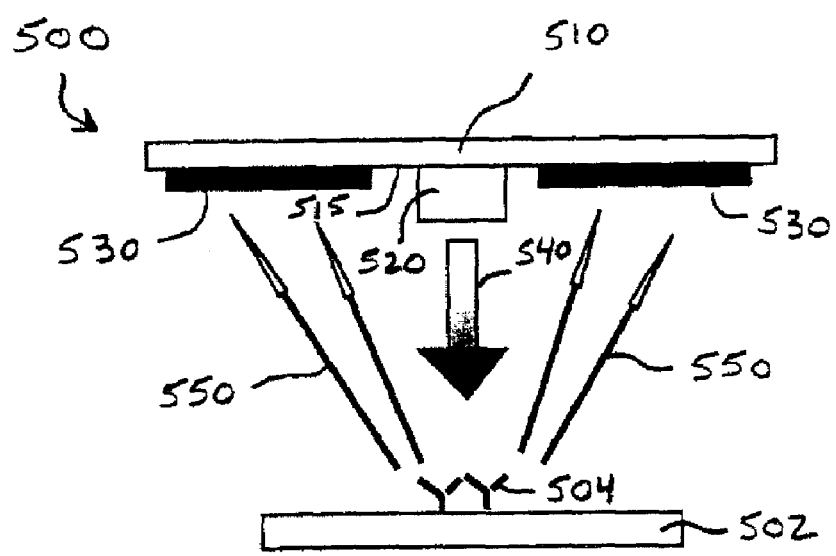
FIG. 5A illustrates a micro-circuit arrangement in a proximity configuration, according to another example embodiment of the present invention.

FIG. 5A shows a micro-circuit arrangement 500 having a proximity architecture for detecting excitable target markers, according to another example embodiment of the present invention. Micro-circuit arrangement 500 includes a substrate 510 having a substrate surface 515. An excitation source 520 is coupled to the substrate surface 515 and adapted to emit a first electromagnetic radiation 540 away from the substrate 510 towards a biochip 502. The first electromagnetic radiation 540 excited a target marker 504 into emitting a second electromagnetic radiation 550 generally back towards substrate 510. In one implementation, biochip 502 is approximately 500 microns from the optical-detector.

A filter/optical-detector 530 includes at least one optical-detector (not individually shown in FIG. 5) and a filter optically coupled to the optical-detector (not individually shown in FIG. 5). Filter/optical-detector 530 is coupled to the substrate surface 515 in proximity to the excitation source 520 and arranged in a planar array with the excitation source 520. Filter/optical-detector 530 is adapted to filter first electromagnetic radiation 540, sense the second electromagnetic radiation 550 and generate a detection signal responsive to sensing the second electromagnetic radiation.

Figure 5B:
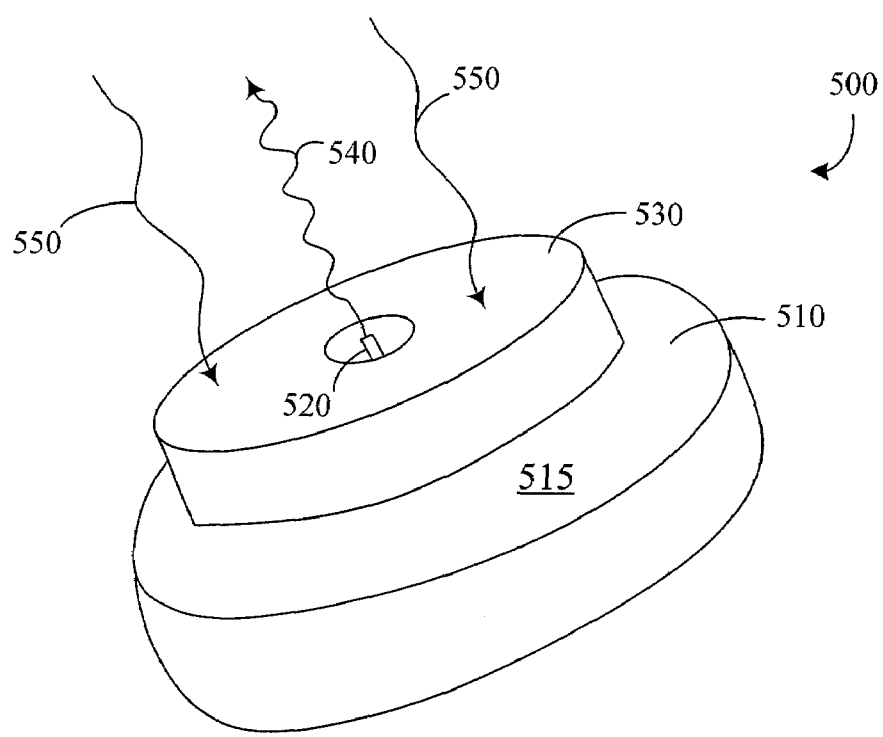
FIG. 5B illustrates a proximity sensor implementation of the micro-circuit arrangement in a proximity configuration of FIG. 5A, according to another example embodiment of the present invention.

Filter/optical-detector 530 may include a plurality of discrete filter/detectors or may be a singular circular filter/optical-detectors surrounding emitter 520, as further illustrated in FIG. 5B (note FIG. 5B shows micro-circuit arrangement 500 inverted from FIG. 5A). The micro-circuit arrangement 500 of FIG. 5B may, for example, be implemented in as a proximity sensor. The proximity architecture of the arrangement 500 facilitates the emissions from the excitation source 520 to propagate freely to a biological sample on the biochip 502. Filter/optical-detector 530 is configured to have a relatively large area with respect to source 520 to collect the resulting fluorescence without aid of a micro-optics structure between arrangement 500 and biochip 502. In this architecture, optical-detector diameter and design are tailored to maximize acceptance angle for fluorescent emission while keeping the laser blocking properties to below a specific value (usually better than $10^4$ rejection).

Figure 6:
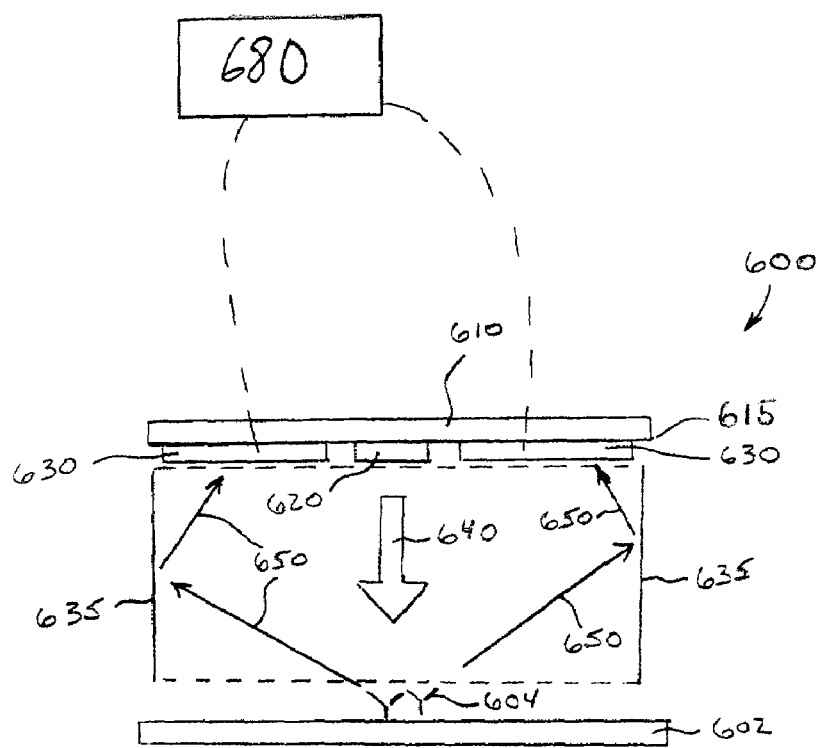
FIG. 6 illustrates a micro-circuit arrangement in a waveguide configuration, according to another example embodiment of the present invention.

FIG. 6 shows a micro-circuit arrangement 600 having a light guide and/or Total Internal Reflection (TIR) architecture for detecting excitable target markers, according to another example embodiment of the present invention. Micro-circuit arrangement 600 includes a substrate 610 having a substrate surface 615. An excitation source 620 is coupled to the substrate surface 615 and adapted to emit a first electromagnetic radiation 640 away from the substrate 610 towards a biochip 602. The first electromagnetic radiation 640 excites a target marker 604 into emitting a second electromagnetic radiation 650 generally back towards substrate 610.

A filter/optical-detector 630 includes at least one optical-detector (not individually shown in FIG. 6) and a filter optically coupled to the optical-detector (not individually shown in FIG. 6). In one implementation, filter/optical detector 630 is a singular, circular filter/optical-detector surrounding emitter 620, for example as illustrated in FIG. 5B. Filter/optical-detector 630 is coupled to the substrate surface 615 in proximity to the excitation source 620 and arranged in a planar array with the excitation source 620. Filter/optical-detector 630 is adapted to filter first electromagnetic radiation 640, sense the second electromagnetic radiation 650 and generate a detection signal responsive to sensing the second electromagnetic radiation.

A light guide structure 635 is located between the biochip 602 and both the emitter 620 and the filter/optical detector 630. The light guide structure 635 reflects escaping second electromagnetic radiation 650 back towards filter/optical-detector 630. The light guide structure 635 includes a multi-mode guide having one or more of various shapes (e.g., round, rectangular, hexagonal). Typical width/length ratios include, but are not limited to, ratios of 1:5 to 1:10 in widths between 50 and 1000 microns on the side. Light guide 635 efficiently tunnels the first electromagnetic radiation 640 (e.g., light) between the source 620 and the target marker 604, and the second electromagnetic 650 radiation back towards the optical-detector 630. This approach facilitates small channel spacing, limits cross talk, and simplifies micro-optics fabrication and alignment. Light guides that may be implemented in connection with this example embodiment are available from Collimated Holes, Inc. of Campbell, Calif.

A circuit arrangement 680 is optionally coupled to one or more portions of the micro-circuit arrangement 600 shown in FIG. 6. The circuit arrangement 680 includes one or more of a plurality of circuit types, such as control, analysis or data recording circuitry that can be used in connection with various aspects of the application of the micro-circuit arrangement 600. For instance, control circuitry such as that used to control a laser or other electromagnetic radiation source may be implemented in connection with circuit arrangement 680. In addition, as discussed further below, the circuit arrangement 680 may include a CPU.

In another embodiment of the present invention, one excitation source with a plurality of discrete filter/optical-detectors is utilized. Each detector is used to monitor a different property of the dye emission that is excited by the excitation source. For example, the detectors could be tailored to detect different colors, which would be useful in experiments involving multi-color dyes. These detectors could be arranged to surround the excitation source. Also, these designs may include the use of micro-optics to increase the amount of emission reaching the detector surface. Micro-optics can also be used to direct emission of a unique color to a specific detector.

According to another embodiment of the present invention, a substrate upon which at least one micro-circuit arrangement (e.g., a one-sided architecture as discussed above) is coupled to a biochip leaving a cavity or channel therebetween. The cavity or channel is adapted for passing biological samples, which pass the sensing features (e.g., source(s) and associated optical-detector(s) as discussed above) of the micro-circuit arrangement. The biological sample containing target markers is pumped through the channel where it is tested by at least one, one-sided architecture of the present invention.

According to another aspect of the present invention, a plurality of micro-circuit arrangements each detect excitable target markers in response to an excitation source. Each micro-circuit arrangement functions as a pixel, the plurality of pixels being in proximity to another and in a substantially planar distribution on a circuit foundation (e.g., in an array). Assimilation circuitry monitors each such pixel, or each optical-detector of each pixel. The excitation source of each pixel emits a first electromagnetic radiation to excite one or more target markers into emitting a second electromagnetic radiation. At least one corresponding filter is adapted to attenuate the first electromagnetic radiation from being sensed by the optical-detectors of each pixel. Each optical-detector arrangement is adapted to sense the second electromagnetic radiation and generate detection signals in response to sensing the second electromagnetic radiation.

The assimilation circuitry functions as a decoder to report data indicative of the likely target and/or reporting one of the optical-detectors. This reported data can be then further analyzed manually or automatically through additional equipment such as a programmed CPU. According to one example implementation, an analog to digital converter converts the signals generated by the optical-detectors to digital signals, and the assimilation circuit includes a microcomputer adapted to receive and process the digital signals and to identify the likely target marker. Furthermore, the assimilation circuitry and/or the CPU associates detection signals to the geographic location of the optical-detectors (or pixels) within the array. Placing a biosample in a known orientation to the array thusly enables determination of the presence of specific target markers attracted to geographically-segregated probes based on the above-described geographic sensing technique.

According to another example embodiment, a plurality of optical-detectors are in proximity to another and in a substantially planar distribution on a circuit foundation (e.g., in an array). Assimilation circuitry monitors each such optical-detector. A independent excitation source, common to all optical-detectors of the array, emits a first electromagnetic radiation to excite one or more target markers into emitting a second electromagnetic radiation. At least one filter corresponding to each optical-detector, or to a group of optical-detectors, is adapted to attenuate the first electromagnetic radiation from being sensed by the corresponding optical-detectors. Each optical-detector arrangement is adapted to sense the second electromagnetic radiation and generate detection signals in response to sensing the second electromagnetic radiation. The assimilation circuitry functions as a decoder to report data indicative of the likely target and/or reporting one of the optical-detectors. This reported data is then further analyzed manually or automatically through additional equipment such as a programmed CPU.

According to one example implementation, a single independent laser simultaneously illuminates an entire biological sample into fluorescence. The fluorescence is thereafter detected by an array of optical-detectors on the same side of the biological sample as the laser. According to another example implementation, a laser source sequentially illuminates a biological sample, for example by scanning over the biological sample. The scanning is repeated in some cycle as necessary to continue excitation of the target markers in the biological sample.

According to another example implementation, an excitation source is combined with several optical-detectors or detection channels, where respective optical-detectors measure or sensing the same or different characteristic of the biological specimen. One portion of the plurality of optical-detectors/filter micro-circuit arrangements are adapted to sense a particular characteristic of a second electromagnetic radiation, and another portion of the plurality of optical-detectors/filter micro-circuit arrangements are adapted to sense a different particular characteristic of the second electromagnetic radiation.

According to a more particular implementation, a plurality of optical-detectors/filters are configured and arranged such that a target marker is presented sequentially to a portion of the plurality of optical-detectors/filters. For example, the target marker flows across a biochip, being sensed by a series of optical-detectors/filters geographically distributed across an array and along the target marker's path. In another example, the target marker remains stationary and the array of optical-detectors/filters is passed near the target marker such that a series of optical-detectors/filters geographically distributed across an array are passed near the target marker over time. In this manner, fluorescence intensity variations in time are measured.

In another example implementation, these optical-detectors are tailored to sense different colors of radiation, useful for multi-dye experiments. Another embodiment has one optical-detector optimized to measure biosample spectra and another optical-detector optimized to measure the excited state lifetime of the biosample, such as in fluorescent lifetime measurement (FLIM), and another optical-detector optimized for detection sensitivity.

According to another example implementation, the excitation source and detector combination are optimized to detect a specific characteristic of the biological specimen. For example, one sensor (i.e., micro-circuit arrangement pixel) is optimized for sensitivity where an adjacent sensor is optimized to measure excited state lifetime. Various combinations and permutations of optical-detector and/or filter and/or excitation source characteristics are contemplated within the scope and spirit of the present invention. Other example implementations are adapted to measure different characteristics to increase detection limits and add system flexibility. In one instance, a plurality of excitation sources are implemented for exciting target markers that respond in a manner relative to different types of excitation characteristics. In another instance, a plurality of filter/detection arrangements, as discussed herein, are adapted for detecting different types of electromagnetic radiation that are related to different characteristics of target markers (e.g., to different characteristics of a biosample).

Figure 7:
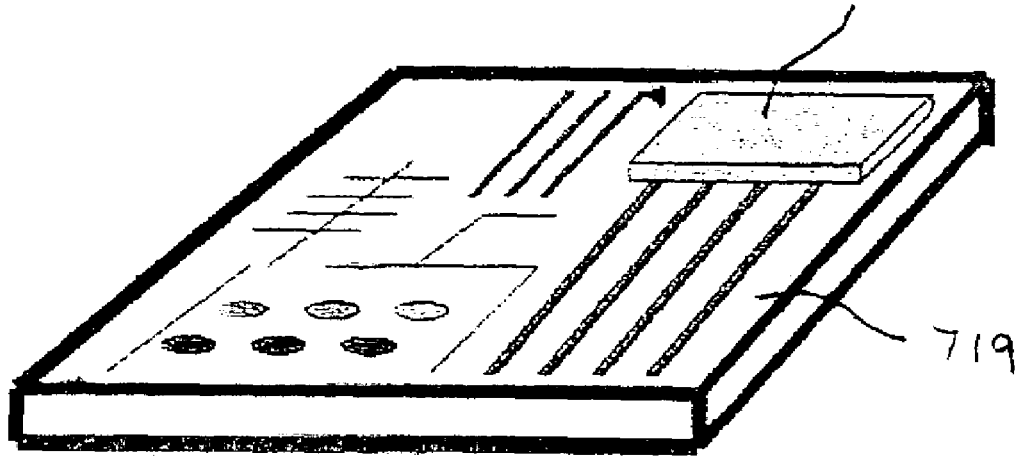
FIG. 7 illustrates a micro-total analytical system including a micro-circuit arrangement, according to another example embodiment of the present invention.

FIG. 7 illustrates a micro-total analysis system (µTAS) 718, according to another example embodiment of the present invention. The µTAS 718 includes an integrated circuit chip 700 having at least one micro-circuit arrangement for detecting excitable target markers as described above. The sensing chip 700 is coupled to the biochip 719. According to one implementation, a plurality of micro-circuit arrangements are logically coupled in a parallel or pixilated architecture to perform bio-analysis on a relatively large biological sample. According to another implementation, parallel sensing architectures of more than one hundred channels provide high throughput experimentation using parallel flow channels for faster processing.

In another implementation, an array of sensors is arranged in a common plane having a pixel/sensor pitch of 200 microns. For example, a 1×10 or 1×50 sensor array is capable of monitoring parallel capillaries. The µTAS 718 is bio-processor, or lab chip, used for analyzing biological samples and may contain flow channels and perform functions such as capillary array electrophoresis, hybridization, etc. A portable µTAS has applications including, but not limited to, clinical medicine laboratory techniques (e.g., disease screening), molecular detection, drug research, biological agent field analysis, micro-array readers, and other biological experimentation.

Figure 8:
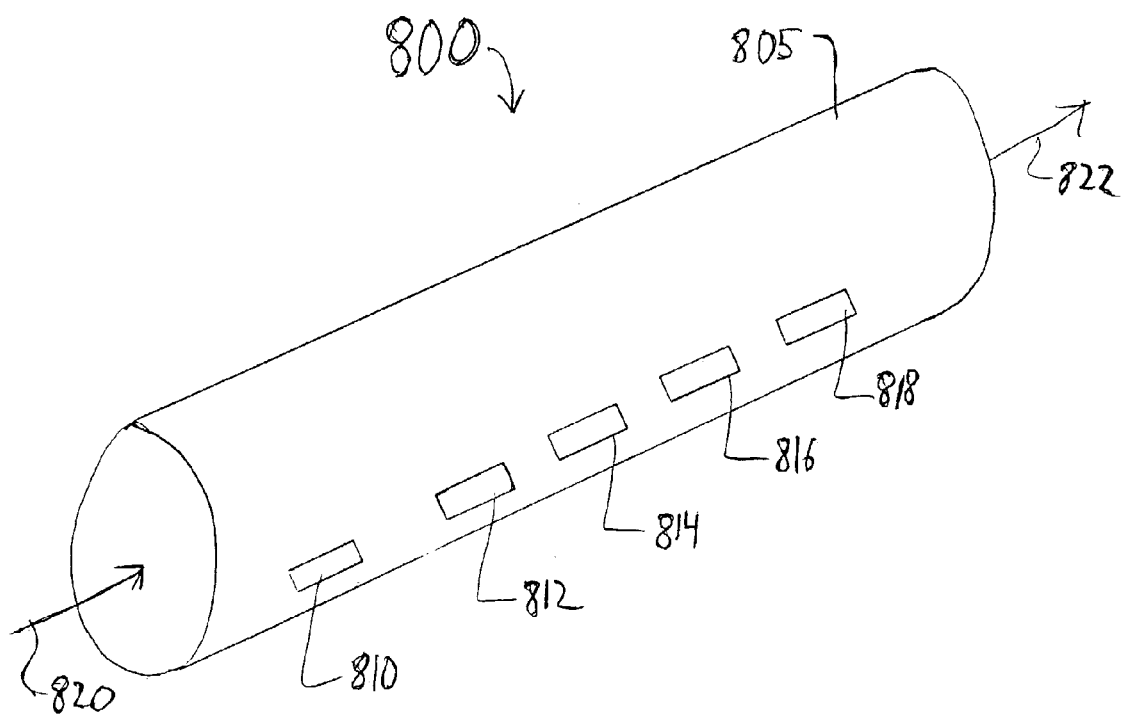
FIG. 8 shows a plurality of micro-circuit arrangements in a channel through which samples flow, according to another example embodiment of the present invention.

FIG. 8 shows an arrangement 800 having a channel 805 with a plurality of micro-circuit arrangements 810, 812, 814, 816 and 818 therein and adapted for detecting characteristics of material flowing through the channel 805, as represented by input arrow 820 and output arrow 822. The micro-circuit arrangements may, for example, include one or more of the emission and filter/optical detection arrangements discussed above. For instance, referring to FIG. 1, one or more of micro-circuit arrangement 100 may be implemented in the flow channel 805 to detect the flow of biological samples passing by. Aspects of the material flowing through the channel that may be detected, for example, include flowrate, concentration and identity of the materials.

Figure 9:
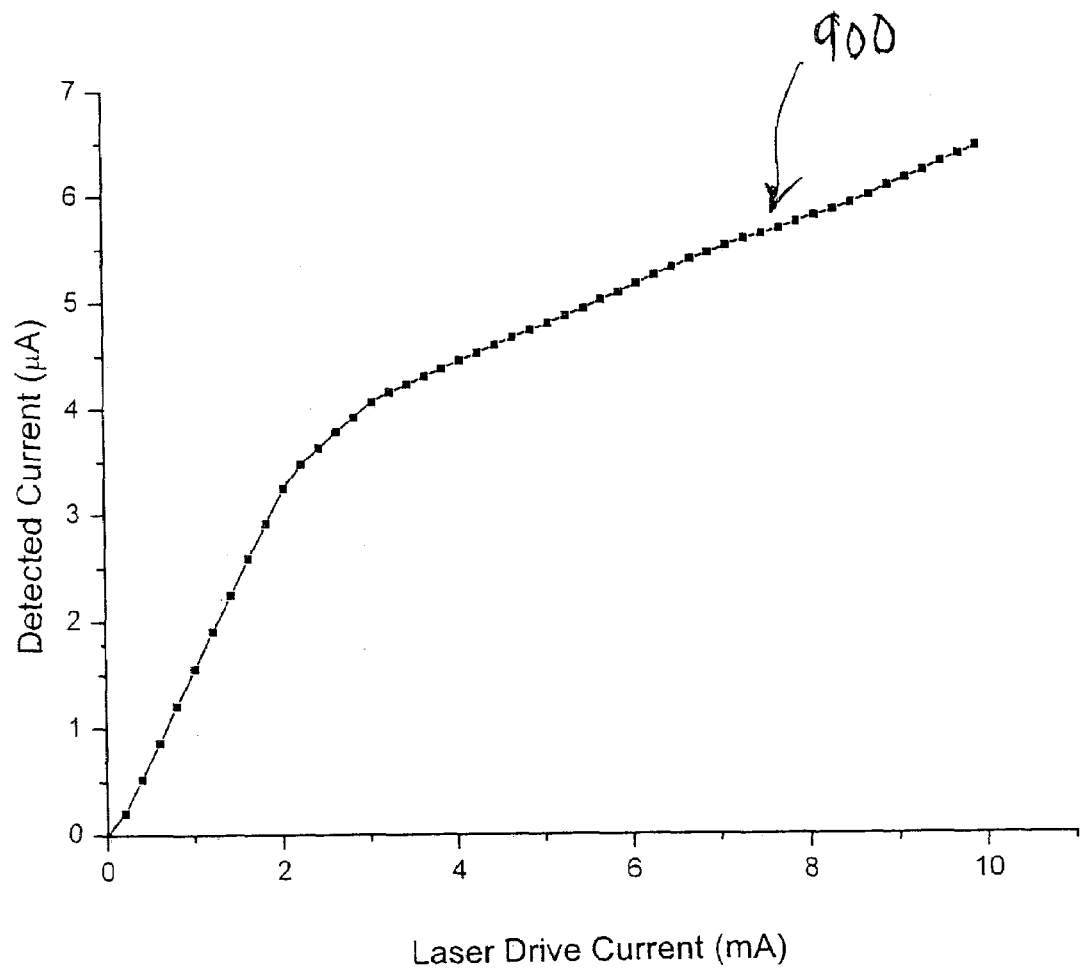
FIG. 9 shows a plot of detected current versus drive current, to which various example embodiments of the present invention are directed to reducing.

FIG. 9 shows a plot 900 for emission background caused by a VCSEL, to which various example embodiments of the present invention are directed to reducing. The plot 900 shows current relative to detected emissions (e.g., using a photodetector) on the vertical axis and Laser (VSCEL) drive current on the horizontal axis. A kink in the curve is shown at the laser threshold (about 2 mA), which results because above the threshold, most of the drive current goes into a laser mode that propagates vertically and does not interact with the detector. Below 2 mA (threshold), spontaneous emission out the side of the VCSEL grows strongly with input drive current. In one implementation, a photodetector with absorbing and/or highly reflective materials (e.g., metal or some type of interference filter) is used to reduce the amount of detected current. In another implementation, a mesa photodetector is used with a DBR interference filter deposited on top of the photodetector to reduce the amount of detected emissions.

In another example embodiment of the present invention, a source filter near the excitation source (e.g., having absorbing and/or reflecting medium) is adapted to mitigate and/or prevent stray emissions from the excitation source. For instance, with a filter arrangement having a pinhole-type opening therein, the direction of the emissions can be controlled, reducing the angular distribution of the emissions. With this approach, the emissions can be directed to a particular location (i.e., a target marker) while limiting stray emissions from undesirably reaching a detector.

Figure 10:
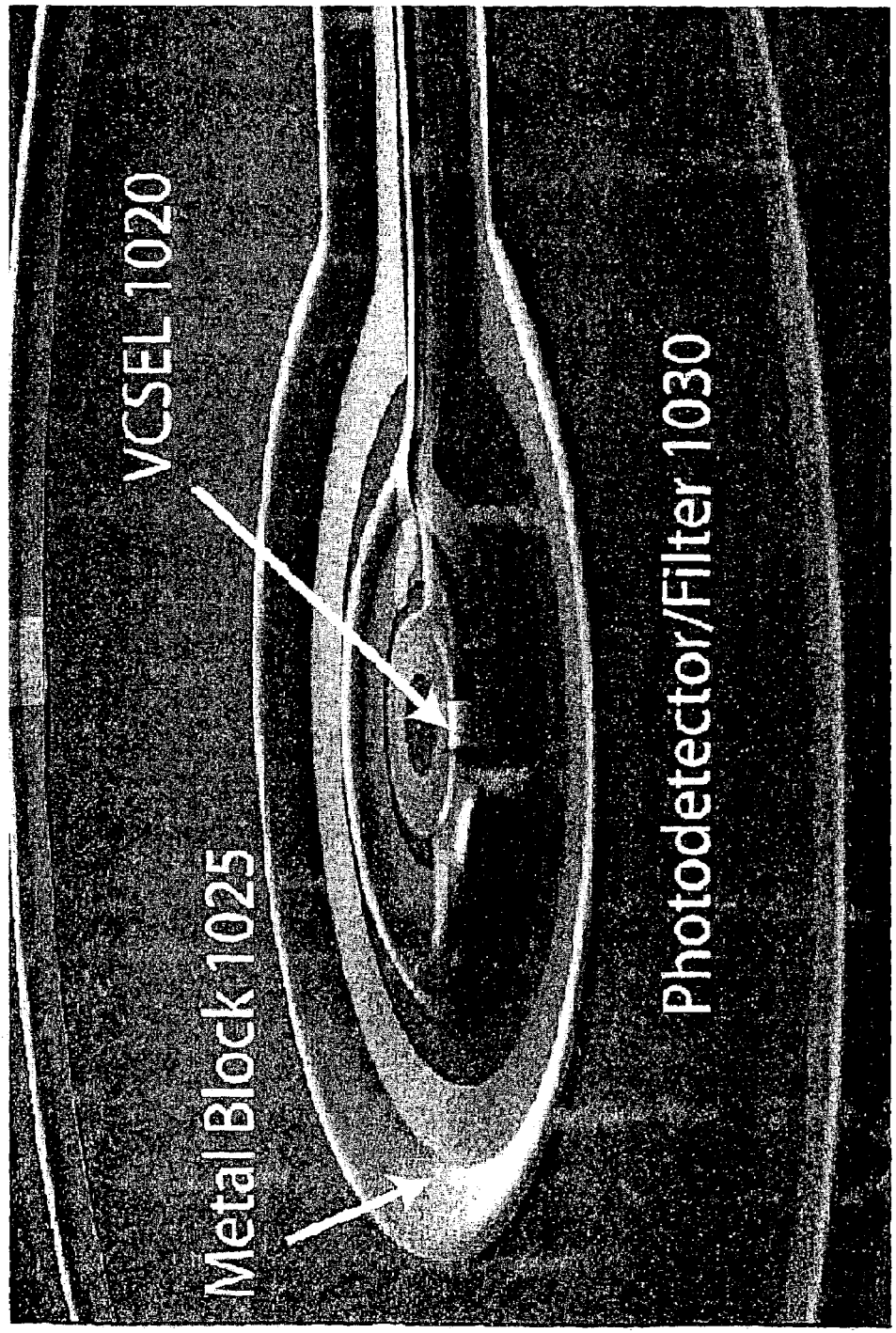
FIG. 10 shows a source/detector arrangement with an emission blocking arrangement between a source and detector, according to another example embodiment of the present invention.

FIG. 10 shows a source/detector arrangement 1000 including metal blocking layer 1025 (i.e., a source filter as discussed above) placed between a VCSEL excitation source 1020 and mesa photodetector 1030, according to another example embodiment of the present invention. The Metal blocking layer 1025 is adapted to attenuate or block emissions from the VCSEL excitation source 1020 from reaching the photodetector/filter 1030. Specifically, the metal blocking layer 1025 blocks stray emissions from the VCSEL excitation source 1020 from traveling laterally toward the photodetector/filter 1030. For instance, the shape and location of the metal blocking layer 1025 is selected to reflect stray emissions from the VCSEL excitation source 1020 up and away from the photodetector/filter 1030. The metal blocking layer 1025 extends laterally between the VCSEL excitation source 1020 and the photodetector/filter 1030, as well as above the VCSEL excitation source and the photodetector/filter, relative to the direction of the emissions. The curved structure of the metal blocking layer 1025, as well as the height thereof (in the direction of the emissions from the VCSEL excitation source 1020), directs emissions reflecting therefrom in a direction generally away from the photodetector/filter 1030.

In another example embodiment of the present invention, a source filter includes a blocking layer (e.g., metal or an absorbing medium, such as a doped polymer) formed over an optoelectronic device, such as those shown in FIG. 10. When the blocking layer includes conductive material, an insulative material such as cured positive photoresist is placed between the optoelectronic device and the blocking layer to electrically insulate them from one another. Openings in the blocking layer are formed using processes such as etching and photolithography. Emissions can pass from an excitation source and/or to a detector under the blocking layer vie the openings, while the amount of stray emissions from the excitation source that can reach the detector are reduced or eliminated with the blocking layer. With this approach, the blocking layer can be conformed to underlying structure, which is useful for forming the blocking layer over three-dimensional structure.

In one implementation involving conductive and/or non-conductive material in the blocking layer, a spacing layer (e.g., an insulative layer) is formed over the optoelectronic device to achieve a particular arrangement of the blocking layer. For example, it is sometimes desirable to elevate the blocking layer over an emission source. In this regard, the spacing layer is formed extending over the emission source such the blocking layer, when formed on the spacing layer, is elevated over the emission source.

Figure 11:
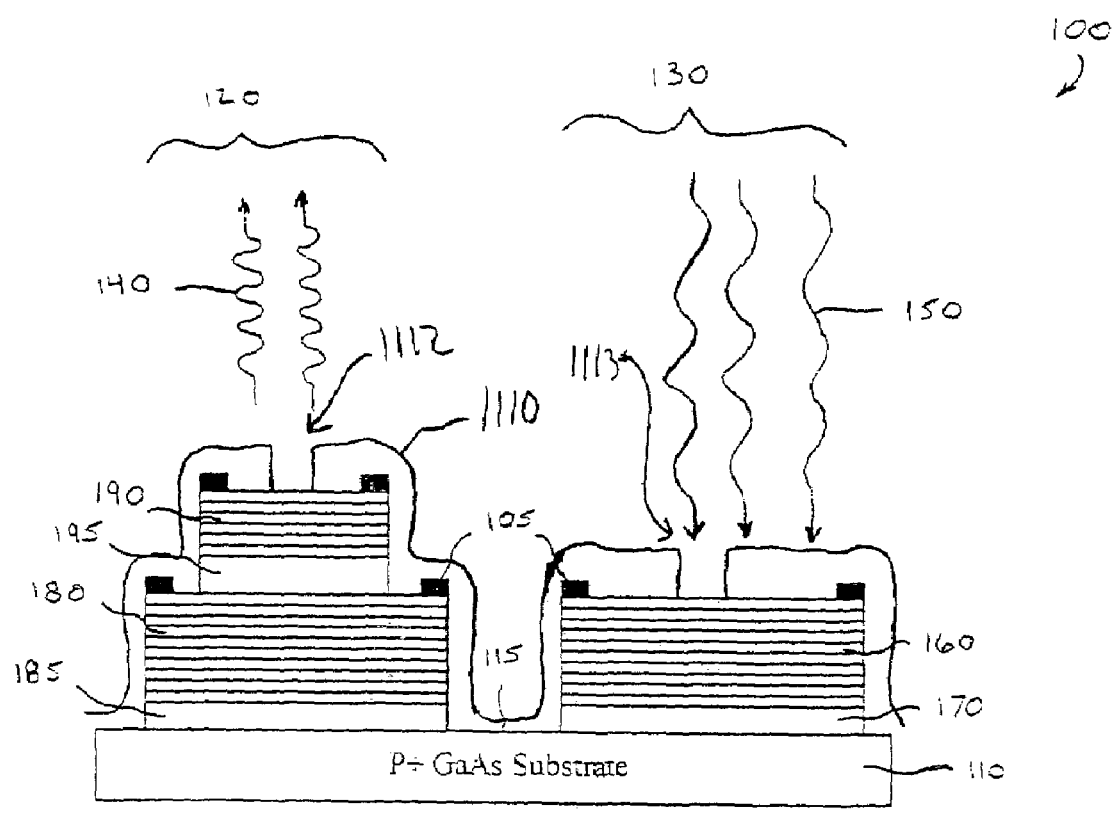
FIG. 11 shows the micro-circuit arrangement of FIG. 1 having a blocking layer thereon adapted to reduce emissions from a source that reach a detector, according to another example embodiment of the present invention.

FIG. 11 shows one particular implementation of a blocking layer as discussed above, with a blocking layer 1110 extending over the micro-circuit arrangement 100 shown in FIG. 1, according to another example embodiment of the present invention. Small openings 1112 and 1113 in the blocking layer 1110 permit first electromagnetic emission 140 to pass from the light emitter 120 towards a target marker and also permit second electromagnetic radiation 150 to pass to the filter/optical detector 130.

Figure 12:
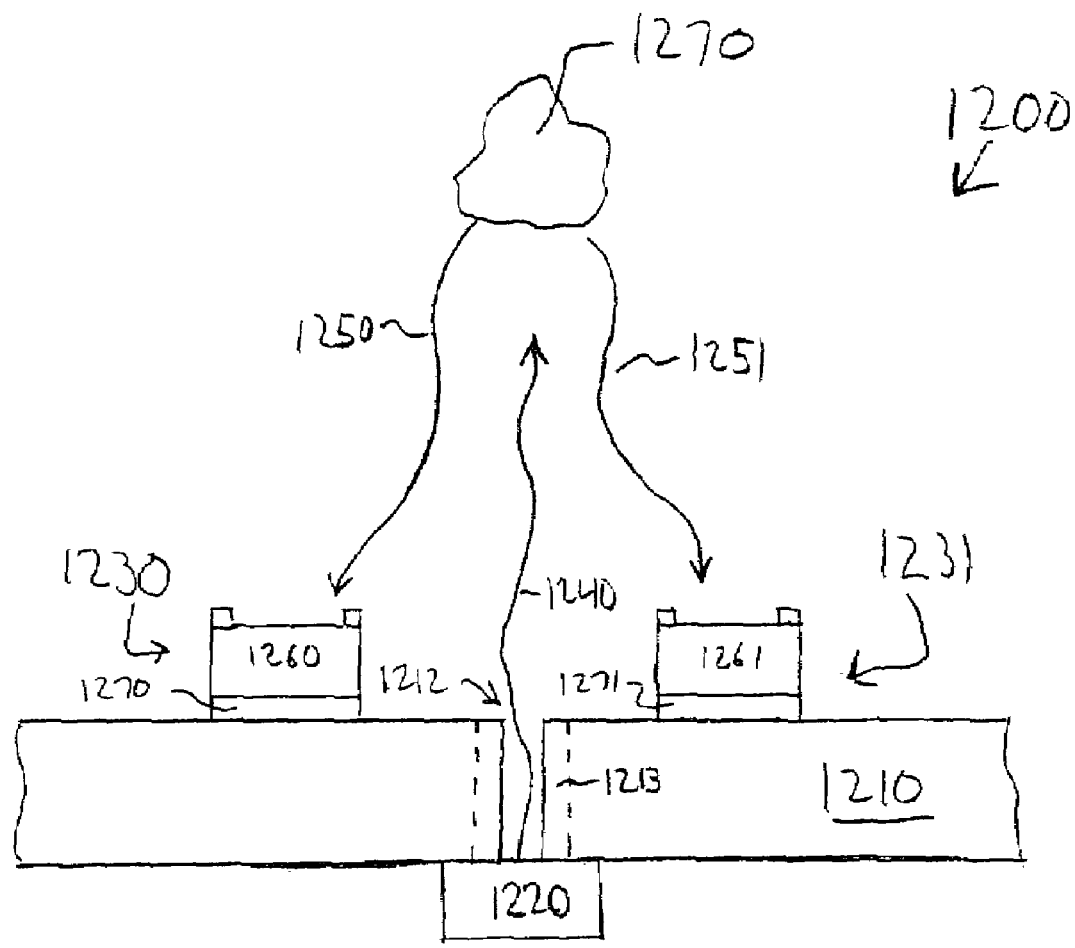
FIG. 12 shows a cross-sectional view of an approach and arrangement for reducing stray emissions that reach a detector, according to another example embodiment of the present invention.

FIG. 12 shows a cross-sectional view of another approach to reducing the amount stray emissions from an emission source that reach a detector, according to another example embodiment of the present invention. A target marker detection arrangement 1200 includes an emitter 1220 and detectors 1230 and 1231 formed on a substrate 1210 (e.g., a GaAs substrate, similar to substrate 110 of FIG. 1). The detectors 1230 and 1231 may, for instance, be implemented using an approach similar to that shown in FIG. 1, with filters 1260 and 1261 and optical detectors 1270 and 1271, respectively. The emitter 1220 is adapted to emit primary emission 1240 towards a target marker 1270 through a pinhole region 1212 in the substrate 1210. In response to the primary emission 1240, the target marker 1270 emits secondary emissions 1250 and 1251, which are detected by the detectors 1260 and 1261. The substrate 1210 absorbs emissions from the emission source 1220 that are not directed in a generally normal direction from the substrate 1210, thereby reducing portions of the emission 1240 that reach the detectors 1260 and 1261. In one implementation, the substrate 1210 includes material selected to absorb emissions from the emitter 1220. In a more particular implementation, portions of the substrate 1210 near the pinhole 1212 include a material that is different than material in other portions of the substrate 1210 (e.g., formed by doping portion 1213 of the substrate 1210 around the pinhole 1212 to increase absorbing characteristics thereof).

While the present invention has been described with reference to several particular example embodiments, those skilled in the art will recognize that many changes may be made thereto without departing from the spirit and scope of the present invention. The present invention is applicable to a variety of biosensor applications and other subject matter, in addition to those discussed above. For general information regarding sensor and other implementations, and for specific information regarding approaches to which one or more of the various example embodiments and implementations discussed above may be applicable, reference may be made to the attached references set forth below. For instance, reference may be made to one or more of the following U.S. Pat. Nos. 5,914,976, 5,936,730, 5,978,401, 6,097,748, 6,197,503 and 6,344,644 for more information regarding optical electronic devices and approaches that may be applicable for implementation in connection with one or more example embodiments of the present invention. Similarly, reference may be made to one or more of the '730 and '503 references for more information regarding biosensing devices and approaches that may be applicable for implementation in connection with one or more example embodiments of the present invention. In this regard, each of the above patent documents is fully incorporated herein by reference.

What is claimed is:

1. An array of micro-circuit arrangements for detecting excitable target markers located in an external medium, the array comprising:
    a foundation layer having a first surface; and
    a plurality of micro-circuit arrangements coupled to the first surface in proximity to one another and arranged in an array, each micro-circuit arrangement including:
        an excitation source coupled to the first surface, and adapted to emit a first respective electromagnetic radiation in a direction predominately away from the foundation layer to excite a respective target marker into emitting a second respective electromagnetic radiation;
        at least one corresponding optical-detector coupled to the first surface in proximity to the excitation source and arranged in the array with the excitation source, the at least one corresponding optical-detector adapted to sense the second respective electromagnetic radiation from a second direction opposite the first direction and generate a respective detection signal responsive to sensing the respective second electromagnetic radiation; and
        a filter optically coupled to the at least one corresponding optical-detector, the filter being arranged and configured to attenuate the first respective electromagnetic radiation from being sensed by the at least one corresponding optical-detector;
    wherein first and second groups of the plurality of micro-circuit arrangements are configured differently based on at least one of: ability to sense fluorescence decay of the target marker at first and second times, respectively; and different filter responses provided respectively by the first and second groups of the plurality of micro-circuit arrangements.

2. The array of claim 1, wherein each of the at least one corresponding optical detectors are adapted to sense a common second electromagnetic radiation.

3. The array of claim 2, wherein one portion of the plurality of micro-circuit arrangements is adapted to sense a particular characteristic of the common second corresponding electromagnetic radiation, and another portion of the plurality of micro-circuit arrangements are adapted to sense a different particular characteristic of the common second corresponding electromagnetic radiation.

4. The array of claim 3, wherein the plurality of micro-circuit arrangements are configured and arranged to sequentially present a target marker as the respective target marker to a portion of the plurality of micro-circuit arrangements.

5. An array of micro-circuit arrangements for detecting excitable target markers located in an external medium, the array comprising:
    a foundation layer having a first surface; and
    a plurality of micro-circuit arrangements coupled to the first surface in proximity to one another and arranged in an array, each micro-circuit arrangement including:
        an excitation source coupled to the first surface, and adapted to emit a first respective electromagnetic radiation in a direction predominately away from the foundation layer to excite a respective target marker into emitting a second respective electromagnetic radiation;
        at least one corresponding optical-detector coupled to the first surface in proximity to the excitation source and arranged in the array with the excitation source, the at least one corresponding optical-detector adapted to sense the second respective electromagnetic radiation from a second direction opposite the first direction and generate a respective detection signal responsive to sensing the respective second electromagnetic radiation; and
    a filter optically coupled to the at least one corresponding optical-detector, the filter being arranged and configured to attenuate the first respective electromagnetic radiation from being sensed by the at least one corresponding optical-detector, wherein one portion of the plurality of micro-circuit arrangements are configured to sense fluorescence decay of the target marker at a first time, and another portion of the plurality of micro-circuit arrangements are configured to sense fluorescence decay of the target marker at a second time.

6. The array of claim 5, further comprising a target marker detection channel structure adapted to pass the target marker sequentially between portions of the plurality of micro-circuit arrangements over time.

7. The array of claim 1, wherein the second respective electromagnetic radiation excited and sensed by a portion of the plurality of micro-circuit arrangements has different characteristics from the second respective electromagnetic radiation excited and sensed by another portion of the plurality of micro-circuit arrangements.

8. The array of claim 1, wherein a portion of the plurality of micro-circuit arrangements includes corresponding optical detectors that are adapted to sense a second respective electromagnetic radiation having different characteristics from the second respective electromagnetic radiation sensed by corresponding optical detectors included in another portion of the plurality of micro-circuit arrangements.

9. The array of claim 1, wherein a portion of the plurality of micro-circuit arrangements includes filters having a different filter response from the filter response of filters included in another portion of the plurality of micro-circuit arrangements.

10. The array of claim 1, wherein at least a portion of the plurality of micro-circuit arrangements is arranged in a channel through which particles flow and adapted to detect a molecular flowrate of particles through the channel.

* * * * *

UNITED STATES PATENT AND TRADEMARK OFFICE
CERTIFICATE OF CORRECTION

PATENT NO.        : 7,604,981 B1
APPLICATION NO.   : 10/384166
DATED             : October 20, 2009
INVENTOR(S)       : Harris, Jr. et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1885 days.

Signed and Sealed this

Fifth Day of October, 2010

David J. Kappos
*Director of the United States Patent and Trademark Office*